United States Patent [19]

Bosies et al.

[11] Patent Number: 4,687,767

[45] Date of Patent: Aug. 18, 1987

[54] CERTAIN 1-HYDROXYETHANE, 1,1-DI-PHOSPHONIC ACID DERIVATIVES USEFUL IN TREATING CALCIUM METABOLISM DISTURBANCES

[75] Inventors: Elmar Bosies, Weinheim; Rudi Gall, Hirschberg, both of Fed. Rep. of Germany

[73] Assignee: Boehringer Mannheim GmbH, Mannheim, Fed. Rep. of Germany

[21] Appl. No.: 759,608

[22] Filed: Jul. 26, 1985

[30] Foreign Application Priority Data

Aug. 2, 1984 [DE] Fed. Rep. of Germany ....... 3428524

[51] Int. Cl.$^4$ .......................... C07F 9/58; C07F 9/65; A61K 31/44; A61K 31/415
[52] U.S. Cl. ........................ 514/89; 514/80; 514/92; 514/93; 514/94; 548/112; 548/113; 548/115; 546/22
[58] Field of Search .................. 548/112; 546/22; 514/89, 94

[56] References Cited

U.S. PATENT DOCUMENTS 4,503,049  3/1985  Biere et al. ........................... 514/80

FOREIGN PATENT DOCUMENTS 0084822  8/1983  European Pat. Off. .............. 514/80
0085321  8/1983  European Pat. Off. .............. 514/95
1813659  7/1969  Fed. Rep. of Germany ...... 558/163

Primary Examiner—Alan L. Rotman
Attorney, Agent, or Firm—Felfe & Lynch

[57] ABSTRACT

The present invention provides diphosphonates of the general formula:

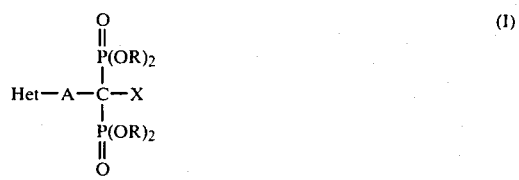

wherein Het is an imidazole, oxazole, isoxazole, thiazole, pyridine, 1,2,3-triazole, 1,2,4-triazole or benzimidazole radical, which is optionally substituted by alkyl, alkoxy, halogen, hydroxyl, carboxyl, an amino group optionally substituted by alkyl or alkanoyl radicals or a benzyl radical optionally substituted by alkyl, nitro, amino or aminoalkyl, A is a straight-chained or branched, saturated or unsaturated hydrocarbon chain containing 2 to 8 carbon atoms, X is a hydrogen atom, optionally substituted by alkanoyl, or an amino group optionally substituted by alkyl or alkanoyl radicals and R is a hydrogen atom or an alkyl radical; and the pharmacologically acceptable salts thereof.

The present invention also provides processes for the preparation of these diphosphonates and pharmaceutical compositions containing them.

12 Claims, No Drawings

CERTAIN 1-HYDROXYETHANE, 1,1-DI-PHOSPHONIC ACID DERIVATIVES USEFUL IN TREATING CALCIUM METABOLISM DISTURBANCES

The present invention is concerned with new diphosphonic acid derivatives, processes for the preparation thereof and pharmaceutical compositions containing them.

Federal Republic of Germany Patent Specification No. 32 03 308 describes arylethane-diphosphonates, for example thienylethane-diphosphonate, which have an outstanding anti-inflammatory action. European Patent Specification No. 0 084 822 describes, inter alia, pyrazolealkyl-diphosphonates which have an antiarthritic action.

Federal Republic of Germany Patent Specification No. 18 13 659 describes diphosphonic acid derivatives of which 1-hydroxyethane-1,1-diphosphonic acid has achieved importance for the treatment of Paget's disease.

We have now found that analogous derivatives of this compound, in which the alkyl chain is substituted by an aromatic heterocyclic radical, also display this action and, in addition, are well suited as good calcium complex formers for the wider treatment of calcium metabolism disturbances. In particular, they can very well be used in cases where the build up and breakdown of bone is disturbed, i.e. they are suitable for the treatment of diseases of the skeletal system, for example osteoporosis, Paget's disease, Bechterew's disease and the like.

On the basis of these properties, however, they can also be used in the therapy of bone metastases, urolithiasis and for the prevention of heterotopic ossification. Due to their influencing of the calcium metabolism, they also form a basis for the treatment of rheumatoid arthritis, osteoarthritis and degenerative arthrosis.

Thus, according to the present invention, there are provided diphosphonates of the general formula:

wherein Het is an imidazole, oxazole, isoxazole, thiazole, pyridine, 1,2,3-triazole, 1,2,4-triazole or benzimidazole radical, which can optionally be substituted by alkyl, alkoxy, halogen, hydroxyl, carboxyl, an amino group optionally substituted by alkyl or alkanoyl radicals or a benzyl radical optionally substituted by alkyl, nitro, amino, or aminoalkyl, A is a straight-chained or branched, saturated or unsaturated hydrocarbon radical containing 2 to 8 carbon atoms, X is a hydrogen atom, a hydroxyl group optionally substituted by alkanoyl or an amino group optionally substituted by alkyl or alkanoyl radicals and R is a hydrogen atom or an alkyl radical; as well as the pharmacologically acceptable salts thereof.

In all cases, alkyl means itself or in an alkoxy radical a hydrocarbon radical containing up to 4 carbon atoms, the methyl, ethyl and isopropyl radicals being preferred. By alkanoyl radical there is to be understood an alkanoyl radical containing up to 6 carbon atoms, especially a formyl, acetyl, propionyl, butyryl or valeroyl radical, acetyl and propionyl radicals being preferred.

By halogen, there is to be understood fluorine, chlorine, bromine and iodine, chlorine and bromine being preferred.

The chain A preferably means —(CH$_2$)$_n$—, wherein n is 2 to 5,

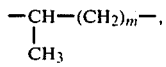

wherein m is 2 to 5, —CH=CH—CH$_2$—CH$_2$—, —CH=CH—CH$_2$—CH$_2$—CH$_2$—and—CH=CH—CH=CH—, the saturated radicals being especially preferred.

The substituent X is preferably hydroxyl or amino, hydroxyl being especially preferred.

The compounds of general formula (I) can be prepared by known processes.

For the case in which X in general formula (I) is a hydroxyl group, the compounds are preferably prepared in that:

(a) a carboxylic acid of the general formula:

in which Het and A have the above-given meanings, is reacted with a mixture of phosphorous acid and a phosphorus halide and subsequently saponified to the free diphosphonic acid, or (b) a carboxylic acid chloride of the general formula:

in which Het and A have the above-given meanings, is reacted with a trialkyl phosphite of the general formula:

in which R' is a lower alkyl radical, to give an acyl phosphonate of the general formula:

in which Het, A and R' have the above-given meanings, subsequently reacted with a dialkyl phosphite of the general formula:

in which R' has the above-given meaning, to give a diphosphonate of the general formula:

in which Het, A and R' have the above-given meanings, and the resultant tetraester optionally saponified to diesters or acids of general formula (I) or for the case in which X in general formula (I) is an amino group optionally substituted by alkyl radicals, (c) a carboxylic acid derivative of the general formula:

$$Het—A—Z \quad (VIII),$$

in which Het and A have the above-given meanings and Z is a nitrile, imino ether or an N,N-dialkylcarboxamido radical, is reacted with a phosphorus compound of the general formula:

$$PT_3 \quad (IX),$$

in which T is halogen, hydroxyl or OR', R' having the above-given meaning, and optionally subsequently saponified, or for the case in which X in general formula (I) is a hydrogen atom (d) a compound of the general formula:

$$Het—A—Y \quad (X),$$

in which Het and A have the above-given meanings and Y is a reactive residue, for example halogen or sulphonate, is reacted with a compound of the general formula:

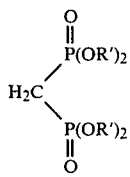

(XI)

in which R' has the above-given meaning, to give a diphosphonate of the general formula:

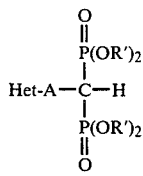

(XII)

in which Het, A and R' have the same meanings as above, and the resulting tetraester optionally saponified to diesters or acids of general formula (I).

The carboxylic-acids of general formula (II) used in process (a) are reacted with 1 to 2 and preferably 1.5 mole of phosphorous acid and 1 to 2 and preferably 1.5 mole of phosphorus trihalide at a temperature of from 80° to 130° C. and preferably of from 100° to 110° C. The reaction can also be carried out in the presence of diluents, for example halogenated hydrocarbons, especially chlorobenzene or tetrachloroethane, or also dioxan. The subsequent hydrolysis can be carried out by boiling with water but preferably with semi-concentrated hydrochloric or hydrobromic acid. Phosphorus acid and phosphorus trihalide may be substituted in this reaction by phosphorus pentoxide, phosphorus-pentahalide respectively phosphorus oxi-halide. (DE-A No. 21 30 794, DE-A No. 26 58 961, DE-A No. 27 02 631 and DE-A No. 29 43 498)

In the case of process (b), the acid chloride of general formula (III) is reacted with the trialkyl phosphite of general formula (IV) at a temperature of from 0° to 60° C. and preferably of from 20° to 40° C. It is possible to work without the use of a solvent or also in the presence of inert solvents, for example diethyl ether, tetrahydrofuran, dioxan or also halogenated hydrocarbons, for example methylene chloride. The acyl phosphonate of general formula (V) formed as intermediate can be isolated or also further reacted directly. The subsequent reaction is carried out in the presence of a weak base, preferably a secondary amine, such as dibutylamine, at a temperature of from 0° to 60° C. and preferably of from 10° to 30° C.

In the case of process (c), the nitriles of general formula (VIII) are reacted with phosphorous acid at a temperature of from 110° to 180° C. The reaction can be carried out without the use of a solvent or in the presence of an aprotic solvent, for example diglycol dimethyl ether or diglycol diethyl ether. However, the nitriles can also be reacted with a phosphorus trihalide, for example phosphorus tribromide or phosphorus trichloride, in an inert solvent, for example dioxan or tetrahydrofuran, possibly with the addition of water, at a temperature of from 20° to 80° C. Imino ethers of general formula (VIII) can be reacted with dialkyl phosphites, preferably in the presence of equimolar amounts of sodium, in inert solvents, such as diethyl ether, dioxan or also benzene, whereby, as a rule, the reaction takes place at the reflux temperature of the solvent used. Acid amides of general formula (VIII) can be reacted in inert solvents, for example halogenated hydrocarbons or ethers, for example diethyl ether, with a mixture of a phosphorus pentahalide/phosphorous acid or also of oxalyl chloride/trialkyl phosohite.

In the case of process (d), the methylenediphosphonic acid ester of general formula (XI) is used in the form of its sodium or potassium salt. For this purpose, it is reacted with sodium, potassium or the corresponding hydride in an inert solvent, for example benzene, toluene or dimethylformamide, at a temperature of from 0° to 40° C. and preferably at 25° C. The alkali salt is reacted, without isolation, with the appropriate halide or sulphonate. The temperature is hereby from 20° to 110° C.

The tetraalkyl esters possibly obtained in the case of processes (b), (c) and (d) can be saponified to diesters or to the free tetraacids. The saponification to diesters takes place, as a rule, by treating the tetraalkyl esters with an alkali metal halide, preferably sodium iodide, in an appropriate solvent, for example acetone, at ambient temperature. There is hereby formed the symmetrical diester/disodium salt which can possibly be converted by means of an acidic ion exchanger into the diester/diacid.

As a rule, the saponification to free diphosphonic acids takes place by boiling with hydrochloric or hydrobromic acid. However, a splitting can also be carried with a trimethylsilyl halide, preferably the bromide or iodide. On the other hand, the free diphosphonic acids can again be converted into the tetraalkyl esters by boiling with orthoformic acid alkyl esters. The free diphosphonic acids of general formula (I) can be isolated as free acids or in the form of their mono- or dialkali metal salts. As a rule, the alkali metal salts can be readily purified by reprecipitation from water/methanol or water/acetone.

The compounds of general formula (I) can possibly be subsequently converted from one into another. For example, they can be alkylated or acylated or, when X in general formula (I) is an unsubstituted amino group, can be converted by diazotisation into compounds of general formula (I) in which X is a hydroxyl group. By means of hydrogenolytic splitting off of an N-benzyl radical, there can be prepared, for example, the corresponding unsubstituted compounds of general formula (I).

As pharmacologically acceptable salts, there are used, in particular, the alkali metal or ammonium salts which are prepared in conventional manner, for example by neutralisation of the compounds with inorganic or organic bases, for example sodium or potassium hydrogen carbonate, aqueous sodium hydroxide solution, aqueous potassium hydroxide solution, aqueous ammonia solution or with amines, for example trimethylamine or triethylamine.

The new compounds of general formula (I) according to the present invention and the salts thereof can be administered enterally and parenterally in liquid or solid form. There can hereby be used all conventional forms of administration, for example tablets, capsules, dragees, syrups, solutions, suspensions and the like. As injection medium, it is preferred to use water which contains the additives usual in the case of injection solutions, such as stabilising agents, solubilising agents and buffers. Such additives include, for example, tartrate and citrate buffers, ethanol, complex formers (such as ethylenediaminetetraacetic acid and the nontoxic salts thereof) and high molecular weight polymers (such as liquid polyethylene oxide) for viscosity regulation. Liquid carriers for injection solutions must be sterile and are preferably placed into ampoules. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening materials.

The dosaging can depend upon various factors, such as the mode of administration, species, age and/or individual conditions. The doses to be administered daily are about 1 to 1000 mg/human and preferably 10 to 200 mg/human and can be taken one or more times.

Preferred compounds according to the present invention, apart from the compounds mentioned in the following Examples and the compounds derivable therefrom by combination of the substituents having the meanings given in the claims, include the following diphosphonates:

1-hydroxy-5-(1H-2-imidazolyl)-pentane-1,1-diphosphonic acid
1-hydroxy-3-(1,2H-5-methylimidazolin-2-on-4-yl)-propane-1,1-diphosphonic acid
1-hydroxy-4-(1,3H-5-methylimidazolin-2-on-4-yl)-butane-1,1-diphosphonic acid
1-hydroxy-5-(1,3H-5-methylimidazolin-2-on-4-yl)-pentane-1,1-diphosphonic acid
3-(1,3,5-trimethylimidazolin-2-on-4-yl)-1-hydroxypropane-1,1-diphosphonic acid
4-(1,3,5-trimethylimidazolin 2-on-4-yl)-1-hydroxybutane-1,1-diphosphonic acid
5-(1,3,5-trimethylimidazolin-2-on-4-yl)-1-hydroxypentane-1,1-diphosphonic acid
1-hydroxy-3-(1,2,4-triazol-3-yl)-propane-1,1-diphosphonic acid
1-hydroxy-5-(1,2,4-triazol-3-yl)-pentane-1,1-diphosphonic acid
1-hydroxy-4(1,2,4-triazol-1-yl)-butane-1,1-diphosphonic acid
1-hydroxy-4-(1,2,3-triazol-4-yl)-butane-1,1-diphosphonic acid
1-hydroxy-4-(1-methyl-1,2,3-triazol-4yl)-butane-1,1-diphosphonic acid
4-(1-benzyl-1,2,3-triazol-4-yl)-1-hydroxybutane-1,1-diphosphonic acid
3-(5-amino-1,2,3-triazol-4-yl)-1-hydroxypropane-1,1-diphosphonic acid
5-(5-amino-1,2,3-triazol-4-yl)-1-hydroxypentane-1,1-diphosphonic acid
3-(5-amino-1-methyl-1,2,3-triazol-4-yl)-1-hydroxypropane-1,1-diphosphonic acid
5-(5-amino-1-methyl-1,2,3-triazol-4-yl)-1-hydroxypentane-1,1-diphosphonic acid
3-(5-amino-1-benzyl-1,2,3-triazol-4-yl)-1-hydroxypropane-1,1-diphosphonic acid
5-(5-amino-1-benzyl-1,2,3-triazol-4-yl)-1-hydroxypentane-1,1-diphosphonic acid
1-hydroxy-3-(1,2,3-triazol-1-yl)-propane 1,1-diphosphonic acid
1-hydroxy-5-(1,2,3-triazol-1-yl)-pentane-1,1-diphosphonic acid
3-(2-amino-4-methyl-5-thiazolyl)-1-hydroxypropane-1,1-diphosphonic acid
4-(2-amino-4-methyl-5-thiazolyl)-1-hydroxybutane-1,1-diphosphonic acid
5-(2-amino-4-methyl-5-thiazolyl)-1-hydroxypentane-1,1-diphosphonic acid
1-hydroxy-3-(2-thiazolyl)-propane-1,1-diphosphonic acid
1-hydroxy-3-(4-thiazolyl)-propane-1,1-diphosphonic acid
1-hydroxy-3-(5-thiazolyl)-propane-1,1-diphosphonic acid
3-(2-acetylamino-4-thiazolyl)-1-hydroxypropane-1,1-diphosphonic acid
3-(2-amino-4-thiazolyl)-1-hydroxypropane-1,1-diphosphonic acid
4-(2-amino-4-thiazolyl)-1-hydroxybutane-1,1-diphosphonic acid
5-(2-amino-4-thiazolyl)-1-hydroxypentane-1,1-diphosphonic acid
5-(1-methyl-1,2,3-triazol-4-yl)-1-propionyloxypentane-1,1-diphosphonic acid
5-(1-benzyl-1,2,3-triazol-4-yl)-1-propionylpentane-1,1-diphosphonic acid
5-(1-benzyl-1,2,3-triazol-4-yl)-1-hydroxy-2,4-pentadiene-1,1-diphosphonic acid
1-hydroxy-5-(1,2,3-triazol-2-yl)-pentane-1,1-diphosphonic acid
1-hydroxy-4-(1,2,3-triazol-2-yl)-butane-1,1-diphosphonic acid
1-hydroxy-3-(1-methyl-2-benzimidazolyl)-propane-1,1-diphosphonic acid
1-hydroxy-5-(1-methyl-2-benzimidazolyl)-pentane-1,1-diphosphonic acid
3-(5-benzimidazolyl)-1-hydroxypropane-1,1-diphosphonic acid
5-(5-benzimidazolyl)-1-hydroxypentane-1,1-diphosphonic acid
1-hydroxy-3-(2-methyl-5-benzimidazolyl)-propane-1,1-diphosphonic acid
1-hydroxy-5-(2-methyl-5-benzimidazolyl)-pentane-1,1-diphosphonic acid
1-hydroxy-3-(6-methyl-5-benzimidazolyl)-propane-1,1-diphosphonic acid 1-hydroxy-5-(6-methyl-5-benzimidazolyl)-pentane-1,1-diphosphonic acid
3-(2,6-dimethyl-5-benzimidazolyl)-1-hydroxypropane-1,1-diphosphonic acid
5-(2,6-dimethyl-5-benzimidazolyl)-1-hydroxypentane-1,1-diphosphonic acid
5-(2-benzimidazolyl)-1-hydroxypentane-1,1-diphosphonic acid
3-(1,3H-benzimidazolin-2-on-5-yl)-1-hydroxypropane-1,1-diphosphonic acid
5-(1,3H-benzimidazolin-2-on-5-yl)-1-hydroxypentane-1,1-diphosphonic acid
3-(1,3-dimethylbenzimidazolin-2-on-5-yl)-1-hydroxypropane-1,1-diphosphonic acid
5-(1,3-dimethylbenzimidazolin-2-on-5-yl)-1-hydroxypentane-1,1-diphosphonic acid
1-acetoxy-3-(4-imidazolyl)-propane 1,1-diphosphonic acid
1-amino-3-(4-imidazolyl)-propane-1,1-diphosphonic acid
1-dimethylamino-3-(4-imidazolyl)-propane-1,1-diphosphonic acid
1-acetamido-3-(4-imidazolyl)-propane-1,1-diphosphonic acid
3-(4-imidazolyl)-propane-1,1-diphosphonic acid
1-acetoxy-5-[1-benzyl-4-(1,2,3-triazolyl)]-pentane-1,1-diphosphonic acid
1-amino-5-1-benzyl-4-(1,2,3-triazolyl)]-pentane-1,1-diphosphonic acid
5-[1-benzyl-4-(1,2,3-triazolyl)]-1-methylaminopentane-1,1-diphosphonic acid
3-(4-imidazolyl)-1-propionyloxypropane-1,1-diphosphonic acid.
1-Hydroxy-3-(2-methyl-4-thiazolyl)propane-1.1-diphosphonic acid
1-Hydroxy-3-(2-methyl-5-thiazolyl)propane-1.1-diphosphonic acid
1-Hydroxy-3-(2-methyl-4-imidazolyl)propane-1.1-diphosphonic acid
1-Hydroxy-4-(4-imidazolyl)butane-1.1-diphosphonic acid
1-Hydroxy-3-(3-methyl-4-isoxazolyl)propane-1.1-diphosphonic acid
3-(3-Chlor-5-isoxazolyl)-1-hydroxypropane-1.1-diphosphonic acid
1-Hydroxy-3-(3-methoxy-5-isoxazolyl)propane-1.1-diphosphonic acid
1-Hydroxy-3-(2-methyl-4-oxazolyl)propane-1.1-diphosphonic acid
3-(4.5-Dimethyl-2-oxazolyl)-1-hydroxypropane-1.1-diphosphonic acid
4-(4.5-Dimethyl-2-oxazolyl)-1-hydroxybutane-1.1-diphosphonic acid
5-(4.5-Dimethyl-2-oxazolyl)-1-hydroxypentane-1.1-diphosphonic acid
3-(2-Benzyl-4-oxazolyl)-1-hydroxypropane-1.1-diphosphonic acid
5-(2-Benzyl-4-oxazolyl)-1-hydroxypentane-1.1-diphosphonic acid The following Examples illustrate some of the process variants which can be used for the synthesis of the compounds according to the present invention. However, they do not constitute a limitation of the present invention. As a rule, the compounds are obtained as solid products with high melting points, the structures of which have been verified by H- and P-NMR spectroscopy.

EXAMPLE 1

1-Hydroxy-3-(4-imidazolyl)-propane-1,1-diphosphonic acid 3.53 g. (20 mMol) 3-(4-imidazolyl)-propionic acid hydrochloride are heated with 2.26 g. phosphorous acid in 10 ml. chlorobenzene to 110° C., while stirring. 4.12 g. (30 mMol) phosphorus trichloride are slowly added dropwise thereto and heating continued for 4 hours at 110° C. After cooling, the chlorobenzene is decanted off and the residue boiled under reflux for 5 hours with 15 ml. 6N hydrochloric aci. The reaction mixture is allowed to cool, mixed with active charcoal, filtered and the filtrate evaporated. The residue is taken up in 10 ml. water, the solution is adjusted with an aqueous solution of sodium bicarbonate to a pH value of 5.5 and mixed with methanol until no further precipitate is formed. The precipitate is filtered off with suction, washed with methanol and dried. There are obtained 3.23 g. (48% of theory) of the title compound. The product is obtained as the monosodium salt with 1 mole of water of crystallisation.

In an analogous manner, there are obtained the following compounds by the use of:

(a) 3-(3-pyridyl) -propionic acid:
1-hydroxy-3-(3-pyridyl)-propane-1,1-phosphonic acid in a yield of 25% of theory. The product is obtained as the monosodium salt with 1.5 moles of water of crystallisation.

(b) 3-[1-benzyl-4-(1,2,3-triazolyl)]-propionic acid (m.p. 110°-112° C.; prepared by hydrogenation of 3-[1-benzyl-4-(1,2,3-triazolyl)]-acrylic acid):
3-[1-benzyl-4-(1,2,3-triazolyl)]-1-hydroxypropane-1,1-diphosphonic acid in a yield of 48% of theory. The product is obtained as the dosodium salt with 1 mole water of crystallisation.

(c) 5-[1-benzyl-4-(1,2,3-triazolyl)]-valerianic acid (m.p. 84°-85° C.; prepared by hydrogenation of 5-[1-benzyl-4-(1,2,3-triazolyl)]-2,4-pentadienoic acid):
5-[1-benzyl-4-(1,2,3-triazolyl)]-1-hydroxypentane-1,1-diphosphonic acid in a yield of 53% of theory. The product is obtained as the disodium salt with 1 mole of water of crystallisation.

(d) 3-(4-pyridyl)-propionic acid:
1-hydroxy-3-(4-pyridyl)-propane-1,1-diphosphonic acid in a yield of 56% of theory. The product is obtained as the monosodium salt with 2 moles water of crystallisation.

(e) 3-(2-pyridyl)-propionic acid:
1-hydroxy-3-2-pyridyl)-propane-1,1-diphosphonic acid in a yield of 54% of theory. The product is obtained as the monosodium salt with 2 moles water of crystallisation.

(f) 3-(2-benzimidazolyl)-propionic acid:
3-(2-benzimidazolyl)-1-hydroxypropane 1,1-diphosphonic acid in a yield of 24% of theory. The product is obtained as the monosodium salt with 1.5 moles water of crystallisation.

(g) 5-(1-methyl-1,2,3-triazol-4-yl)-valerionic acid (m.p. 74°-76° C.):
1-hydroxy-5-(1-methyl-1,2,3-triazol-4-yl)-pentane-1,1-diphosphonic acid in a yield of 36% of theory. The product is obtained as the disodium salt with 2 moles water of crystallisation.

(h) 3-(1-methyl-1,2,3-triazol-4-yl)-propionic acid:
1-hydroxy-3-(1-methyl-1,2,3-triazol-4-yl)-propane-1,1-diphosphonic acid in a yield of 50% of theory. The product is obtained as the disodium salt with 2 moles water of crystallisation.

(i) 3-(1-ethyl-1,2,3-triazol-4-yl)-propionic acid:

3-(1-ethyl-1,2,3-triazol-4-yl)-hydroxypropane-1,1diphosphonic acid in a yield of 54% of theory. The product is obtained as the disodium salt with 1 mole water of crystallisation.

(j) 3-[1-(4-methylbenzyl)-1,2,3-triazol-4-yl]-propionic acid:

1-hydroxy-3-[1-(4-methylbenzyl)-1,2,3-triazol-4-yl]-propane-1,1-diphosphonic acid in a yield of 40% of theory. The product is obtained as the disodium salt with 1.5 moles water of crystallisation.

(k) 3-[1-(4-aminomethylbenzyl)-1,2,3-triazol-4-yl]-propionic acid (m.p. 207°-210° C.; prepared by catalytic hydrogenation of 3-[1-(4-cyanobenzyl)-1,2,3-triazol-4-yl]-acrylic acid (m.p. 168°-170° C.) which is obtained by oxidation of the corresponding 3-[1-(4-cyanobenzyl)-1,2,3-triazol-4-yl]-acrolein (m.p. 152°-155° C.)):

3-[1-(4-aminomethylbenzyl)-1,2,3-triazol-4-yl]-1-hydroxypropane-1,1-diphosphonic acid in a yield of 41% of theory. The product is obtained as the disodium salt with 1 mole water of crystallisation.

(l) 3-[1-(3-nitrobenzyl)-1,2,3-triazol-4-yl]-propionic acid (m.p. 147°-150° C.; prepared by reduction by means of hydroxylamine-O-sulphonic acid of 3-[1-(3-nitrobenzyl)-1,2,3-triazol-4-yl]-acrylic acid (m.p. 155°-158° C.), which is obtained by oxidation of the corresponding 3-[1-(3-nitrobenzyl)-1,2,3-triazol-4-yl]-acrolein (m.p. 136°-140° C.):

1-hydroxy-3-[1-(3-nitrobenzyl)-1,2,3-triazol-4-yl]-propane-1,1-diphosphonic acid in a yield of 22% of theory. The product is obtained as the disodium salt with 2 moles water of crystallisation.

(m) 3-(1,2,4-triazol-1-yl)-propionic acid:

1-hydroxy-3-(1,2,4-triazol-1-yl)-propane-1,1-diphosohonic acid in a yield of 45% of theory. The product is obtained as the disodium salt with 1.5 moles water of crystallisation.

(n) 3-(1,2,4-triazole-1-yl)-butyric acid:

1-hydroxy-3-(1,2,4-triazol-1-yl)-butane-1,1-diphosphonic acid in a yield of 44% of theory. The product is obtained as the disodium salt with 1.5 moles water of crystallisation.

(o) 5-(1,2,4-triazol-1-yl)-valerianic acid:

1-hydroxy-5-(1,2,4-triazol-1-yl)-pentane-1,1-diphosphonic acid in a yield of 53% of theory. The product is obtained as the disodium salt with 1.5 moles water of crystallisation.

(p) 3-(1-benzylimidazol-2-yl)-propionic acid:

3-(1-benzylimidazol-2-yl)-1-hydroxypropane-1,1-diphosphonic acid in a yield of 71% of theory. The product is isolated as the free acid with the m.p. 230°-232° C. (foaming up).

EXAMPLE 2

1-Hydroxy-3-[4-(1,2,3-triazolyl)]-propane-1,1-diphosphonic acid.

1 g. 3-[1-benzyl-4-(1,2,3-triazolyl)]-1-hydroxypropane-1,1-diphosphonic acid (see Example 1 (b)) is dissolved in 40 ml. water and hydrogenated at ambient temperature in the presence of 0.5 g. 10% palladium on charcoal. The take up of hydrogen is finished after about 6 hours. The catalyst is filtered off with suction, the filtrate is evaporated, dried and the residue is triturated with methanol. There are obtained 0.74 g. (99% of theory) of the title compound. The product is obtained as the monosodium salt with 1 mole water of crystallisation.

In an analogous manner, there are obtained by the hydrogenation of:

(a) 5-[1-benzyl-(1,2,3-triazol-4-yl)-1-hydroxypentane-1,1-diphosphonic acid (disodium salt; see Example 1 (c)):

1-hydroxy-5-(1,2,3-triazol-4-yl)-pentane-1,1-diphosphonic acid in a yield of 86% of theory. The product is obtained as the disodium salt with 2 moles water of crystallisation.

(b) 3-(1-benzylimidazol-2-yl)-1-hydroxypropane-1,1-diphosphonic acid (see Example 1 (p)):

1-hydroxy-3-(imidazol-2-yl)-propane-1,1-diphosphonic acid in a yield of 26% of theory; m.p. 238° C. sintering, 240°-244°C. with foaming.

(c) 1-hydroxy-3-[1-(3-nitrobenzyl)-1,2,3-triazol-4-yl]-propane-1,1-diphosphonic acid (disodium salt; see Example 1 (l)):

3-[1-(3-aminobenzyl)-1,2,3-triazol-4-yl]-1-hydroxypropane-1,1-diphosphonic acid in a yield of 60% of theory. The product is obtained as the disodium salt with 2 moles water of crystallisation.

We claim:

1. A diphosphonate compound of the formula:

wherein

Het is a substituted or unsubstituted heterocyclic selected from the group consisting of imidazole, or pyridine, 1,2,4- and wherein the substituents are selected from the group consisting of $C_1$-$C_4$ alkyl, $C_1$-$C_4$ alkoxy, halogen selected from the group consisting of fluorine, chlorine, bromine, iodine; hydroxyl, carboxyl, an amino group optionally substituted by $C_1$-$C_4$ alkyl or alkanoyl with up to 6 carbon atoms; benzyl and benzyl substituted by $C_1$-$C_4$ alkyl, nitro, amino or aminoalkyl with 1 to 4 carbon atoms, A is a straight-chained or branched, saturated or unsaturated hydrocarbon chain containing 2 to 8 carbon atoms, X is a hydrogen atom, hydroxy, or alkanoyl of up to 6 carbon atoms and R is a hydrogen atom or an alkyl of 1 to 4 carbon atoms; or a pharmacologically acceptable salt thereof.

2. A compound according to claim 1 wherein each said alkyl is individually selected from the group consisting of methyl, ethyl and isopropyl.

3. A compound according to claim 8 wherein each said alkanoyl is individually selected from the group consisting of formyl, acetyl, propionyl, butyryl, and valeroyl.

4. A compound according to claim 1 wherein each said alkanoyl is individually selected from the group consisting of formyl, acetyl, propionyl, butyryl, and valeroyl.

5. The compound of claim 1 wherein the halogen is chlorine or bromine.

6. The compound of claim 1 wherein X is hydroxyl.

7. The compound of claim 1 wherein X is amino.

8. The compound of claim 1 wherein A is —(CH$_2$)$_n$— wherein n is 2 to 5,

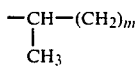

wherein m is 2 to 5, —CH=CH—CH$_2$—CH$_2$—, —CH=CH—CH$_2$—CH$_2$—CH$_2$— or —CH=CH—CH=CH—.

9. A pharmaceutical composition for the treatment of calcium metabolism disorders containing an effective amount of the diphosphonate according to claim 1 for the treatment of calcium metabolism disorders, in combination with an inert conventional carrier or adjuvant.

10. A method for the treatment of calcium metabolism disturbances comprising administering to a mammal in need of said treatment an effective amount of a diphosphonate according to claim 1.

11. A pharmaceutical composition according to claim 6 having 1 to 100 mg of the active ingredient.

12. The method according to claim 7 wherein 1 to 100 mg of the diphosphonate, are administered.

* * * * *

UNITED STATES PATENT AND TRADEMARK OFFICE
CERTIFICATE OF CORRECTION

PATENT NO. : 4,687,767

DATED : August 18, 1987

INVENTOR(S) : Elmar Bosies, et al.

It is certified that error appears in the above-identified patent and that said Letters Patent is hereby corrected as shown below:

Column 10, line 50 (i.e., claim 1, line 18 of test):

after "hydroxy" insert -- amino --.

Signed and Sealed this

Twenty-ninth Day of March, 1988

Attest:

DONALD J. QUIGG

*Attesting Officer*    *Commissioner of Patents and Trademarks*